United States Patent [19]

Pagano

[11] Patent Number: 4,763,526
[45] Date of Patent: Aug. 16, 1988

[54] ULTRASONIC WHEEL PROBE WITH IMPROVED ACOUSTIC BARRIER

[76] Inventor: Dominick A. Pagano, 10 Sasqua Trail, Weston, Conn. 06883

[21] Appl. No.: 79,102

[22] Filed: Jul. 29, 1987

[51] Int. Cl.⁴ .......................................... G01N 29/04
[52] U.S. Cl. ........................................................ 73/639
[58] Field of Search .................. 73/644, 639, 635, 625

[56] References Cited

U.S. PATENT DOCUMENTS

| | | | |
|---|---|---|---|
| 4,098,132 | 7/1978 | Mikesell | 73/639 |
| 4,165,648 | 8/1979 | Pagano | 73/625 |
| 4,519,251 | 5/1985 | Dickson | 73/639 |
| 4,615,218 | 10/1986 | Pagano | 73/639 |

Primary Examiner—Stewart J. Levy
Assistant Examiner—Louis M. Arana
Attorney, Agent, or Firm—Lieberman, Rudolph & Nowak

[57] ABSTRACT

This invention relates generally to an ultrasonic wheel probe for rolling along a workpiece to be tested for flaws, having a plurality of ultrasonic acoustic transducers and an acoustic barrier that rest in a coupling fluid. The instant invention comprises an improved means for detecting the distance between the transducer array and the surface of the workpiece.

7 Claims, 4 Drawing Sheets

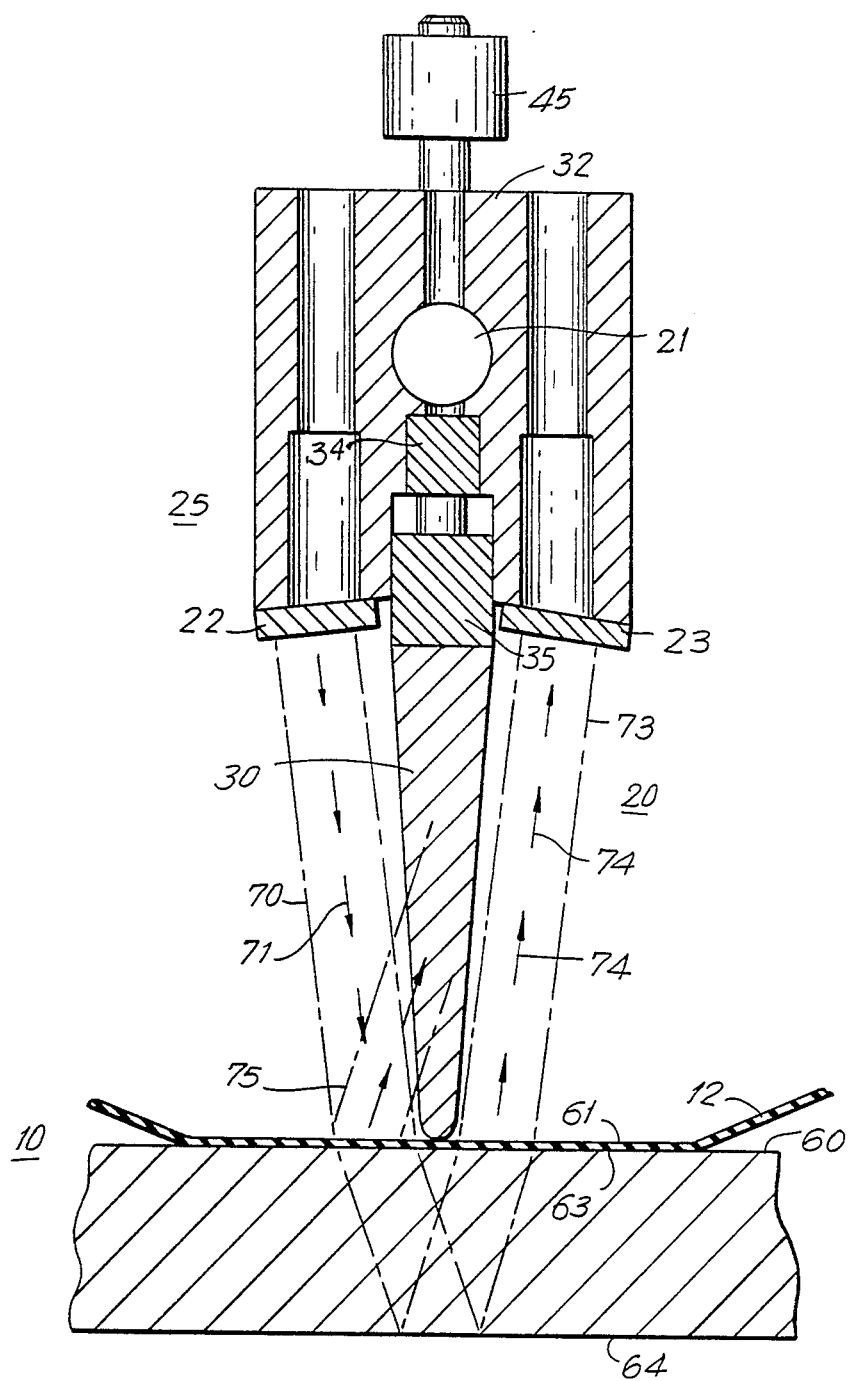

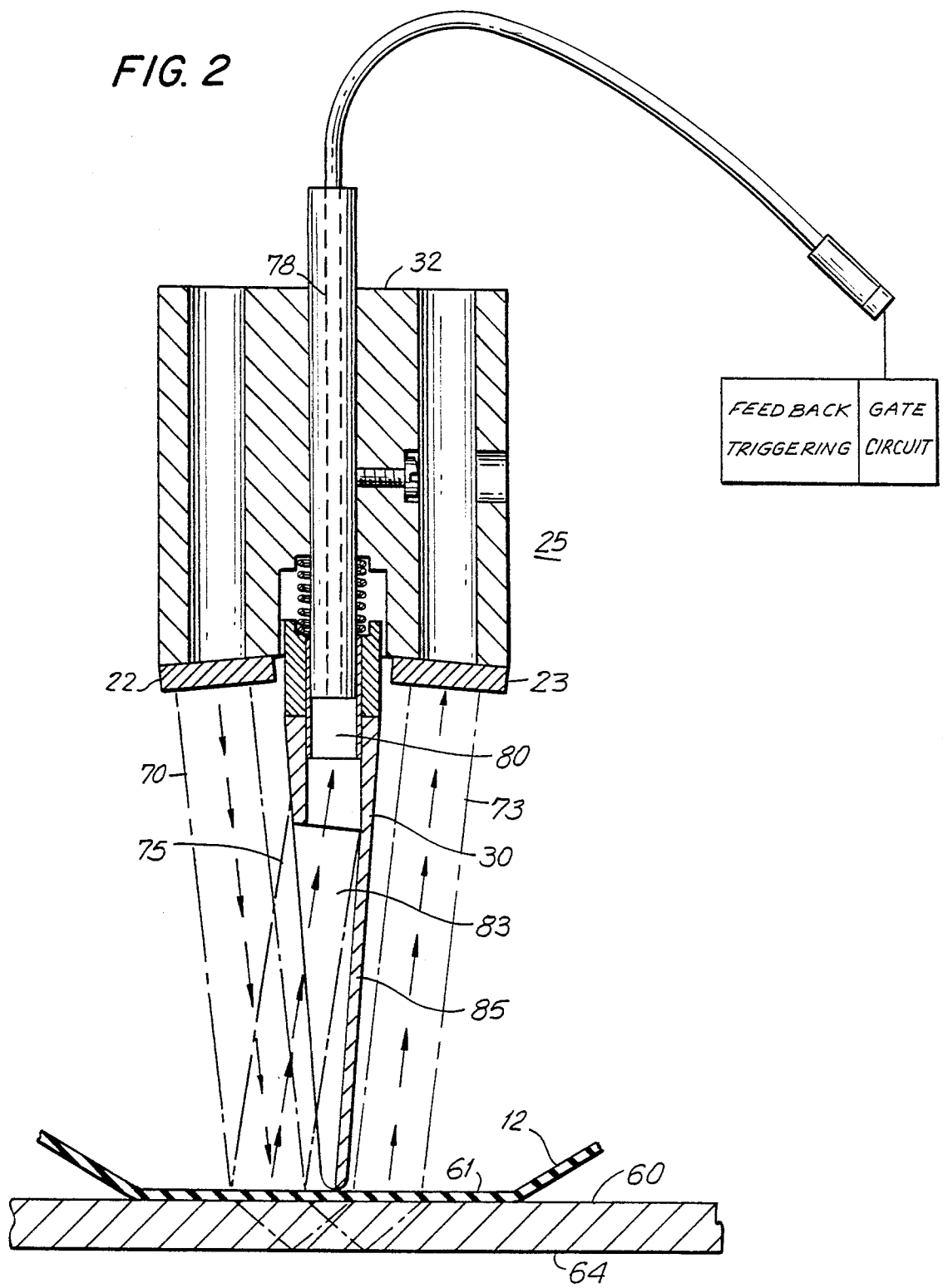

4,763,526

ULTRASONIC WHEEL PROBE WITH IMPROVED ACOUSTIC BARRIER

BACKGROUND OF THE INVENTION

This invention relates generally to ultrasonic testing systems and more particularly, to an ultrasonic wheel probe for rolling along a workpiece to be tested for flaws, having a plurality of ultrasonic acoustic transducers and an acoustic barrier immersed in a coupling fluid. The wheel probe is of the type having a container with a substantially annular outer surface for rotation about an axis of rotation, said wheel probe rolling on a workpiece to be tested, such as a length of pipe.

U.S. Pat. No. 4,615,218 which issued to the applicant herein on Oct. 7, 1986, describes an ultrasonic wheel probe comprised of an acoustic barrier interposed between transmitting and receiving transducers, so as to isolate the transmitting and receiving transducers from one another, thereby preventing crosstalk communication between the transducers which would otherwise occur through the coupling fluid. As described in the patent, the acoustic barrier of one embodiment is mounted on the yoke of the wheel probe so as to extend substantially to an annular inner surface of the container, thereby almost completely sealing the transducers from one another. The acoustic barrier is mounted on the yoke using a resilient, sliding arrangement which permits the distance between the axis of rotation of the container and the outermost extent of the acoustic barrier to be reduced. Thus if the contour of the workpiece being tested requires a deformation of the generally annular outer surface of the container or wheel, then the acoustic barrier can be retracted somewhat to accommodate for such deformation. The transmitting and receiving transducers can be angled within the container so as to permit focusing of the ultrasonic signal at a substantially predeterminable depth within the specimen being tested, the transmitted acoustic energy being propagated through the coupling fluid in a direction which is substantially parallel to, and on one side of, the major plane of the acoustic barrier; which transmitted acoustic energy enters the workpiece and is reflected back along the other side of the acoustic barrier to the receiving transducer. A positional transducer is provided which performs both transmitting and receiving functions and is arranged to transmit its acoustic energy directly to the back of the acoustic barrier, in a direction parallel, and substantially coincident with, the major plane of the acoustic barrier. Yhe reflected signal from the acoustic barrier to the positional transducer corresponds to the position of the acoustic barrier as it is retracted and extended in accordance with the deformation of the outer surface of the wheel probe container, thus monitoring the position of the acoustic barrier. Feedback triggering circuitry can be coupled to the positional transducer so as to define time periods during which echoes resulting from defects within the workpiece being tested can be expected to occur. This function can be performed by gating circuitry which is responsive to the feedback triggering circuits, and which can be arranged to eliminate any boundary reflections, thereby removing the need to gate out interference reflections which would otherwise reduce the material thickness that could be tested. Such a self-adjusting system allows critical segments of the workpiece to be tested with relative reliability. The teachings of U.S. Pat. No. 4,615,218 are specifically incorporated by reference herein.

As taught in the applicant's pending applications Ser. Nos. 735,334 filed on May 17, 1985 and 49,161 filed on May 13, 1987, the use of a plurality of transducer pairs in improved arrays can increase the effective footprint of the wheel probe with respect to the workpiece. As this footprint is increased, monitoring the actual distance of the barrier with respect to the surface of the workpiece, becomes more critical. The prior art wheel probe described in the U.S. Pat. No. 4,615,218 uses a transceiving positional transducer to detect the position of the acoustic barrier with respect to the workpiece being measured. The positional transducer transmits a signal to the acoustic barrier. This signal is reflected by a portion of the barrier and the reflected signal is received by the same transducer. From the time interval between transmission of the signal and detection of the echo signal, the position of the barrier and hence the distance from the transducer array to the surface of the workpiece is determined. As long as the footprint of the area being inspected remains small, this method of measuring transducer array to workpiece distance is adequate. However, as the inspection footprint increases due to, iner alia, the use, of multiple transducer pairs within the wheel probe, the topography of the workpiece becomes more critical. If a bump is encountered by the prior art wheel probe, the acoustic barrier shifts position accordingly thereby causing a momentary aberration in the transducer array to surface distance measurement, not representative of the true distance.

It is therefore the object of the present invention to provide a wheel probe with an acoustic barrier, which features an improved method of measuring the distance of the transducers to the surface of the workpiece.

SUMMARY OF THE INVENTION

In the instant invention, the means for measuring the transducer array to surface distance, is isolated from the physical movement of the acoustic barrier. The instant invention therefore represents an improvement in the wheel probe disclosed in the U.S. Pat. No. 4,615,218. Instead of measuring the position of the acoustic barrier by detecting echoed signals from the barrier itself, the instant invention measures the actual distance between the transducer array and the surface of the workpiece. In one embodiment of the instant invention, a small, receive only, monitor transducer is used instead of the transceiving positional transducer described in the U.S. Pat. No. 4,615,218. The acoustic barrier of the instant invention has a trough running substantially from the tip of the barrier contacting the surface of the workpiece to a point proximate to the monitor transducer. This trough acts as a waveguide which fills with coupling fluid and conducts a portion of the echoed signal reflected by the surface of the workpiece in response to the ultrasonic signal transmitted by the inspecting transducers. As in the wheel probe disclosed in the '218 patent, this embodiment of the instant invention comprises a container with a substantially annular surface for rotation about an axis of rotation said wheel probe rolling a workpiece to be tested. A transducer array of transmitting and receiving transducers separated by an acoustic barrier is mounted upon a yoke. The monitor transducer is mounted on a shaft which is fixedly attached to the yoke. The acoustic barrier is slideably spring mounted on the shaft of the monitor transducer and can thereby adjust to the changes in the surface of the workpiece without disturbing the distance measurement. The system is, therefore, less susceptible to surface aberrations in the workpiece. Another advantage of the instant wheel probe is that its use of the monitor transducer in place of the prior art transceiving transducer, eliminates the pulsing signal which was used solely to detect the position of the acoustic barrier. The absence of this extraneous signal permits more gain in the system with an increase in signal to noise ratio.

It is, therefore, a feature of the instant invention that the distance of the surface of the workpiece with respect to the receive and transmitting transducers is measured by using a receive only monitoring transducer.

It is a further feature of the instant invention that the gain, sensitivity, and signal to noise ratio can be increased.

It is a still further feature of the instant invention that workpieces can be inspected more quickly and accurately.

BRIEF DESCRIPTION OF THE DRAWINGS

FIG. 1 is a cross-sectional side view of one embodiment of the prior art wheel probe disclosed in U.S. Pat. No. 4,615,218.

FIG. 2 is a cross-sectional view of the embodiment of the instant invention along line II—II of FIG. 3.

DETAILED DESCRIPTION

Figure 1A:
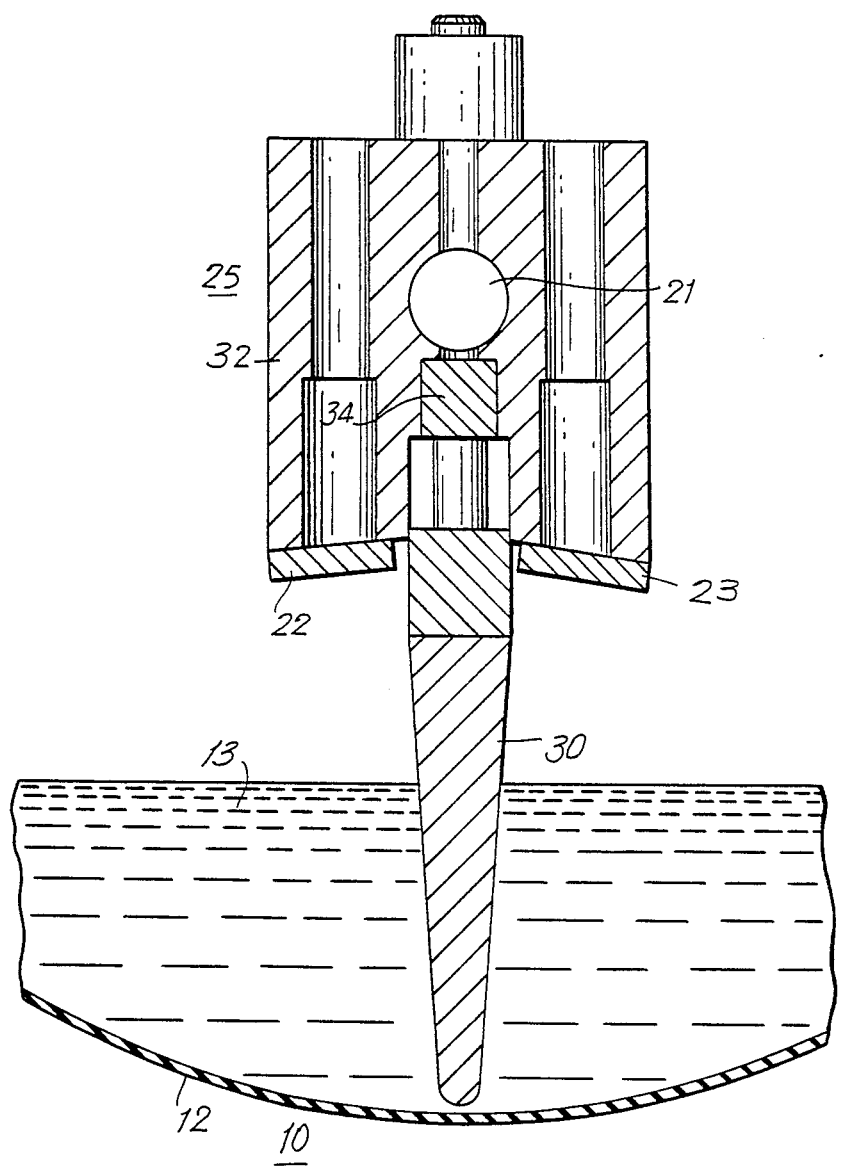
FIG. 1(a) shows the embodiment of FIG. 1 further indicating coupling fluid within the container.
Figure 3:
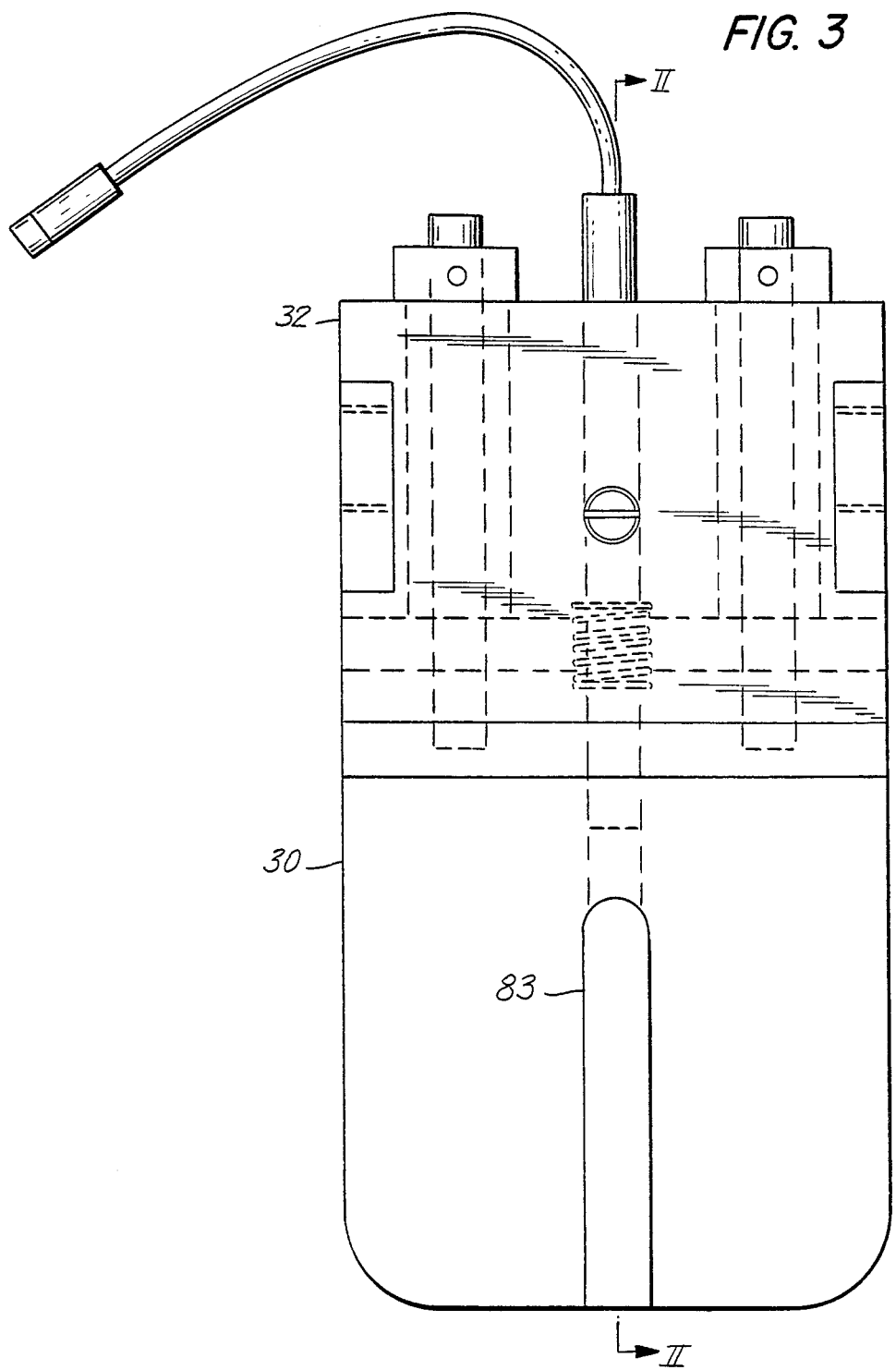
FIG. 3 is a side view of one embodiment of the instant invention.

FIG. 1 is a cross-sectional side view of the prior art wheel probe arrangement 10 constructed in accordance with the principles taught in U.S. Pat. No. 4,615,218, which is incorporated by reference herein. Wheel membrane 12 is shown arranged to encircle a transducer assembly 20 concentrically about an axis of rotation 21 in order to form container 25. As shown in FIG. 1(a), container 25 contains coupling fluid 13. The coupling fluid is present in FIGS. 1, 2, and 3 but for clarity, is not indicated therein. In FIG. 1, membrane 12 is shown flattened where it contacts the surface 63 of workpiece 60. The deformation of wheel membrane 12 in its region 61 where the membrane communicates with workpiece 60, causes a force to be applied upward through acoustic barrier 30 so as to reduce the distance between the axis of rotation 21 and the lowermost extent of acoustic barrier 30. The application of such a force causes barrier mounting member 35 to come closer to positional transducer 34. Positional transducer 34 transmits ultrasonic energy and receives reflections of this energy from barrier mounting member 35. An electrical signal is thereby produced by transducer 34 responsive to the radial location of the acoustic barrier and consequently the distance between transducers 22 and 23 and the surface of workpiece 60. If surface 63 of workpiece 60 has an abberation such as a bump or dimple, the mechanical shifting of barrier 30 will result in an aberrant signal, not truly representative of the distance of transducers 22 and 23 from the workpiece 60. The use of positional transducer 34 to measure the distance between transducers 22 and 23 and the surface of workpiece 60, creates an additional problem in that the distance measuring signal from transducer 34 tends to cause crosstalk when inadvertently detected by transducer 23. This limits the gain which can be used with the system and, therefore, limits the signal to noise ratio.

In order to inspect the workpiece, transmitting transducer transmits a separate beam of ultrasonic energy 70 substantially along an axis of propagation 71. Beam of energy 70 impinges upon a first surface 63 of workpiece 60 and continues to propagate through the workpiece until it reaches a back surface 64 where it is reflected as an echo beam 73 substantially along an axis of propagation 74 and detected by receiving transducer 23. A portion 75 of beam 70 is also reflected by first surface 63. Barrier 30 prevents this reflection 75 from reaching receiving transducer 23 and interfering with echo beam 74.

FIG. 2 is a cross sectional side view of one embodiment of the instant invention representing an improvement over the prior art device described in FIG. 1. Instead of measuring the transducer array to workpiece distance by using a transceiving positional transducer which separately pulses the acoustic barrier, as described in the prior art, the embodiment of the instant invention uses a receive only monitor transducer 80 which detects the reflected portion 75 of beam 70 which is reflected from surface 61 of workpiece 60. Monitor transducer 80 is fixedly mounted to yoke 32 on shaft 78 and barrier 30 is slideably spring mounted upon the supporting shaft 78 so as to compensate for changes in the surface of workpiece 60. A longitudinal trough section is cut in the acoustic barrier 30 forming waveguide 83. The waveguide 83 fills with coupling fluid within container 25 and is shown more clearly in FIG. 3. The waveguide 83 is positioned on the same side of the barrier 30 as the transmitting transducer 22. The waveguide 83 conducts reflected beam 75 to transducer 80 which generates an electrical signal corresponding to the distance of transducers 22 and 23 from surface 61 of workpiece 60. Waveguide 83, although comprising a substantially deep trough, does not penetrate the full width of barrier 30. Portion 85 of the barrier 30 prevents reflected beam 82 from reaching receiving transducer 23 thereby avoiding crosstalk interference with beam 73 reflected from back surface 64.

By utilizing a receive only monitor transducer 80 in the described embodiment of the instant invention, in place of the prior art transceiving transducer, a significant source of noise is eliminated allowing an increase in gain and sensitivity and signal to noise ratio. In addition, the instant embodiment provides a more accurate measurement of the distance between transducers 22 and 23, and surface 61 of workpiece 60, which is less susceptible to aberrations in the surface of the workpiece.

Although the invention has been described in terms of specific embodiments and applications, persons skilled in the art, in light of this teaching, can generate additional embodiments without exceeding the scope or departing from the spirit of the claimed invention, Accordingly, it is to be understood that the drawings and descriptions in this disclosure are proffered to facilitate comprehension of the invention and should not be construed to limit the scope thereof.

What is claimed is:

1. An ultrasonic inspection apparatus of the type having a container with a substantially annular outer surface for rotation about an axis of rotation and rolling on a workpiece to be tested, the container having a yoke arranged at least partly on the axis of rotation and being filled with a coupling fluid for propagating ultrasonic acoustic energy, the ultrasonic inspection apparatus comprising:

first transducer means for transmitting ultrasonic energy through the coupling fluid, the substantially angular outer surface of the container, and into the workpiece to be tested, and second transducer means for receiving echoes of said transmitted ultrasonic acoustic energy;

monitor transducer means fixedly mounted to said yoke for receiving echoes of said transmitted ultrasonic acoustic energy reflected from a first surface of said workpiece;

acoustic barrier means interposed between said first and second transducer means and immersed in the coupling fluid for acoustically isolating said first transducer means from said second transducer means, said acoustic barrier including waveguide means for conducting said first surface echoes of said transmitted ultrasonic acoustic energy to said monitor transducer; and wherein there is further provided mounting means for securing said acoustic barrier means to said yoke, said acoustic barrier means extending substantially to an annular inner surface of the container, said annular inner surface being in communication with the coupling fluid.

2. The ultrasonic inspection apparatus of claim 1 wherein said mounting means further comprises resilient means for extending an outermost extent of said acoustic barrier means substantially to said annular inner surface of the container and for permitting a reduction in a distance between the yoke and said outermost extent of said acoustic barrier means in response to a deformation of the annular outer surface.

3. The ultrasonic inspection apparatus of claim 2 wherein said acoustic barrier is slideably spring mounted upon said monitor transducer means.

4. The ultrasonic inspection apparatus of claim 1 wherein said first and second transducer means are arranged to transmit and receive the ultrasonic acoustic energy along respective axes of propagation, said axes being substantially parallel to a surface of said acoustic barrier means.

5. The ultrasonic inspection apparatus of claim 4 wherein there is further provided feedback triggering means coupled to said monitor transducer means for defining a moment of time after which echoes responsive to flaws within the workpiece being tested are expected to be received by said second transducer means.

6. The ultrasonic inspection apparatus of claim 5 wherein there is further provided gate circuit means having first and second transmission states responsive to said feedback triggering means for transmitting signals responsive to echoes received after said moment of time, and impeding signals responsive to echoes received before said moment of time.

7. The ultrasonic inspection apparatus of claim 6 wherein said signals responsive to echoes received before said moment of time correspond to interface echoes reflected from a surface of the workpiece to be tested.

* * * * *